(12) United States Patent
Gu et al.

(10) Patent No.: US 7,037,683 B2
(45) Date of Patent: May 2, 2006

(54) HUMAN LONGEVITY ASSURANCE PROTEIN, ITS CODING SEQUENCE AND THEIR USE

(75) Inventors: Jianren Gu, Shanghai (CN); Shengli Yang, Shanghai (CN)

(73) Assignee: Shanghai Cancer Institute, Shanghai (CN)

( * ) Notice: Subject to any disclaimer, the term of this patent is extended or adjusted under 35 U.S.C. 154(b) by 0 days.

(21) Appl. No.: 10/389,222

(22) Filed: Mar. 14, 2003

(65) Prior Publication Data

US 2003/0186878 A1 Oct. 2, 2003

Related U.S. Application Data (63) Continuation of application No. PCT/CN01/00105, filed on Jan. 31, 2001.

(30) Foreign Application Priority Data

Sep. 14, 2000 (CN) .......................... 00125197 A (51) Int. Cl.
*A61K 38/17* (2006.01)
*C07K 14/47* (2006.01)

(52) U.S. Cl. .................. 435/69.1; 435/320.1; 435/325; 536/23.5; 530/350

(58) Field of Classification Search ................ 435/69.1, 435/320, 325; 536/23.5; 530/350
See application file for complete search history.

(56) References Cited

U.S. PATENT DOCUMENTS 5,945,330 A * 8/1999 Hillman et al. .......... 435/252.3

FOREIGN PATENT DOCUMENTS

EP   1074617 A2 *   7/2001
WO   WO 00/55350  *   9/2000

OTHER PUBLICATIONS

GenBank, AF189062, Aug. 21, 2000.

* cited by examiner

*Primary Examiner*—Karen Cochrane Carlson
*Assistant Examiner*—Anand Desai
(74) *Attorney, Agent, or Firm*—Dorsey & Whitney LLP (57) ABSTRACT

The present invention relates to a novel human longevity assurance protein, the polynucleotide encoding the polypeptide and a process for producing the polypeptide by recombinant methods. The present invention also relates to a method of applying the polypeptide for the treatment of various kinds of disease, such as cancer. Further, the present invention relates to the antagonist of the polypeptide and therapeutic use of the same. In addition, the present invention includes the use of the polynucleotide encoding the human longevity assurance protein.

5 Claims, 1 Drawing Sheet

SEQUENCE LISTING

<160> NUMBER OF SEQ ID NOS: 3

<210> SEQ ID NO 1
<211> LENGTH: 2007
<212> TYPE: DNA
<213> ORGANISM: Homo sapiens

<400> SEQUENCE: 1

```
ctagaattca gcggccgctg aattctagaa gccgatctag aagaccgaga tggacgtgtc      60
tacgccaaag cctcagatct ctatatcacg ctgcccctgg ccttgctctt cctcatcgtt     120
cgatacttct ttgagctgta cgtggctaca ccactggctg ccctcttgaa cataaaggag     180
aaaactcggc tgcgggcacc tcccaacgcc accttggaac atttctacct gaccagtggc     240
aagcagccca gcaggtggaa gtagagcttt tgtcccggca gagcgggct ctctggccgc     300
caggtagagc gttggttccg tcgccgccgc aaccaggacc ggcccagtct cctcaagaag     360
ttccgagaag ccagctggag attcacattt tacctgattg ccttcattgc cggcatggcc     420
gtcattgtgg ataaaccctg gttctatgac atgaagaaag tttgggaggg atatcccata     480
cagagcacta tcccttccca gtattggtac tacatgattg aactttcctt ctactggtcc     540
ctgctcttca gcattgcctc tgatgtcaag cgaaaggatt tcaaggaaca gatcatccac     600
catgtggcca ccatcattct catcagcttt tcctggtttg ccaattacat ccgagctggg     660
actctaatca tggctctgca tgactcttcc gattacctgc tggagtcagc caagatgttt     720
aactacgcgg gatggaagaa cacctgcaac aacatcttca tcgtcttcgc cattgttttt     780
atcatcaccc gactggtcat cctgcccttc tggatcctgc attgcaccct ggtgtaccca     840
ctggagctct atcctgcctt cttttggctat tacttcttca attccatgat gggagttcta     900
cagctgctgc atatcttctg ggcctacctc attttgcgca tggcccacaa gttcataact     960
ggaaagctgg tagaagatga acgcagtgac cgggaagaaa cagagagctc agaggggag    1020
gaggctgcag ctgggggagg agcaaagagc cggcccctag ccaatggcca ccccatcctc    1080
aataacaacc atcgtaagaa tgactgaacc attattccag ctgcctccca gattaatgca    1140
taaagccaag gaactaccct gctccctgcg ctatagggtc actttaagct ctggggaaaa    1200
aggagaaagt gagaggagag ttctctgcat cctccctcct tgcttgtcac ccagttgcct    1260
ttaaaccaaa ttctaaccag cctatcccca ggtaggggg acgttggtta tattctgtta    1320
gagggggacg gtcgtatttt cctccctacc cgccaagtca tcctttctac tgcttttgag    1380
gccctccctc agctctctgt gggtaggggt tacaattcgc attccttatt ctgagaattt    1440
ggccccagct gtttgccttt gactccctga cctccagagc cagggttgtg ccttattgtc    1500
ccatctgtgg gcctcattct gccaaagctg gaccaaggct aacctttcta agctccctaa    1560
cttgggccag aaaccaaagc tgagctttta actttctccc tctatgacac aaatgaattg    1620
agggtaggag gagggtgcac ataaccctta ccctacctct gccaaaaagt gggggctgta    1680
ctggggactg ctcggatgat cttcttagt gctacttctt tcagctgtcc ctgtagcgac    1740
aggtctaaga tctgactgcc tcctttctct ggcctcttcc cccttccctc ttctcttcag    1800
ctaggctagc tggtttggag tagaatggca actaattcta attttattt attaaatatt    1860
tgggggttttg gttttaaagc cagaattacg gctagcacct agcatttcag cagagggacc    1920
attttagacc aaaatgtact gttaatgggt ttttttttaa aattaaaaga ttaaataaaa    1980
aatattaaat aaaaaaaaaa aaaaaaa                                      2007
```

<210> SEQ ID NO 2
<211> LENGTH: 230
<212> TYPE: PRT
<213> ORGANISM: Homo sapiens

<400> SEQUENCE: 2

```
Met Ala Val Ile Val Asp Lys Pro Trp Phe Tyr Asp Met Lys Lys Val
1               5                   10                  15

Trp Glu Gly Tyr Pro Ile Gln Ser Thr Ile Pro Ser Gln Tyr Trp Tyr
            20                  25                  30

Tyr Met Ile Glu Leu Ser Phe Tyr Trp Ser Leu Leu Phe Ser Ile Ala
        35                  40                  45

Ser Asp Val Lys Arg Lys Asp Phe Lys Glu Gln Ile Ile His His Val
    50                  55                  60

Ala Thr Ile Ile Leu Ile Ser Phe Ser Trp Phe Ala Asn Tyr Ile Arg
65                  70                  75                  80

Ala Gly Thr Leu Ile Met Ala Leu His Asp Ser Ser Asp Tyr Leu Leu
                85                  90                  95

Glu Ser Ala Lys Met Phe Asn Tyr Ala Gly Trp Lys Asn Thr Cys Asn
            100                 105                 110

Asn Ile Phe Ile Val Phe Ala Ile Val Phe Ile Thr Arg Leu Val
            115                 120                 125

Ile Leu Pro Phe Trp Ile Leu His Cys Thr Leu Val Tyr Pro Leu Glu
        130                 135                 140

Leu Tyr Pro Ala Phe Phe Gly Tyr Tyr Phe Phe Asn Ser Met Met Gly
145                 150                 155                 160

Val Leu Gln Leu Leu His Ile Phe Trp Ala Tyr Leu Ile Leu Arg Met
                165                 170                 175

Ala His Lys Phe Ile Thr Gly Lys Leu Val Glu Asp Glu Arg Ser Asp
            180                 185                 190

Arg Glu Glu Thr Glu Ser Ser Glu Gly Glu Glu Ala Ala Ala Gly Gly
        195                 200                 205

Gly Ala Lys Ser Arg Pro Leu Ala Asn Gly His Pro Ile Leu Asn Asn
    210                 215                 220

Asn His Arg Lys Asn Asp
225                 230
```

<210> SEQ ID NO 3
<211> LENGTH: 2007
<212> TYPE: DNA
<213> ORGANISM: Homo sapiens
<220> FEATURE:
<221> NAME/KEY: CDS
<222> LOCATION: (415)..(1104)
<223> OTHER INFORMATION:

<400> SEQUENCE: 3

| | | |
|---|---|---|
| ctagaattca gcggccgctg aattctagaa gccgatctag aagaccgaga tggacgtgtc | 60 |
| tacgccaaag cctcgatatct ctatatcacg ctgcccctgg ccttgctctt cctcatcgtt | 120 |
| cgatacttct ttgagctgta cgtggctaca ccactggctg ccctcttgaa cataaaggag | 180 |
| aaaactcggc tgcgggcacc tcccaacgcc accttggaac attctacct gaccagtggc | 240 |
| aagcagccca gcaggtgga agtagagctt ttgtcccggc agagcgggct ctctggccgc | 300 |
| caggtagagc gttggttccg tcgccgccgc aaccaggacc ggcccagtct cctcaagaag | 360 |
| ttccgagaag ccagctggag attcacattt tacctgattg ccttcattgc cggc atg | 417 |

```
                                                                Met
                                                                 1
gcc gtc att gtg gat aaa ccc tgg ttc tat gac atg aag aaa gtt tgg         465
Ala Val Ile Val Asp Lys Pro Trp Phe Tyr Asp Met Lys Lys Val Trp
         5               10              15 gag gga tat ccc ata cag agc act atc cct tcc cag tat tgg tac tac         513
Glu Gly Tyr Pro Ile Gln Ser Thr Ile Pro Ser Gln Tyr Trp Tyr Tyr
         20              25              30 atg att gaa ctt tcc ttc tac tgg tcc ctg ctc ttc agc att gcc tct         561
Met Ile Glu Leu Ser Phe Tyr Trp Ser Leu Leu Phe Ser Ile Ala Ser
 35              40              45 gat gtc aag cga aag gat ttc aag gaa cag atc atc cac cat gtg gcc         609
Asp Val Lys Arg Lys Asp Phe Lys Glu Gln Ile Ile His His Val Ala
50              55              60              65 acc atc att ctc atc agc ttt tcc tgg ttt gcc aat tac atc cga gct         657
Thr Ile Ile Leu Ile Ser Phe Ser Trp Phe Ala Asn Tyr Ile Arg Ala
             70              75              80 ggg act cta atc atg gct ctg cat gac tct tcc gat tac ctg ctg gag         705
Gly Thr Leu Ile Met Ala Leu His Asp Ser Ser Asp Tyr Leu Leu Glu
             85              90              95 tca gcc aag atg ttt aac tac gcg gga tgg aag aac acc tgc aac aac         753
Ser Ala Lys Met Phe Asn Tyr Ala Gly Trp Lys Asn Thr Cys Asn Asn
             100             105             110 atc ttc atc gtc ttc gcc att gtt ttt atc atc acc cga ctg gtc atc         801
Ile Phe Ile Val Phe Ala Ile Val Phe Ile Ile Thr Arg Leu Val Ile
 115             120             125 ctg ccc ttc tgg atc ctg cat tgc acc ctg gtg tac cca ctg gag ctc         849
Leu Pro Phe Trp Ile Leu His Cys Thr Leu Val Tyr Pro Leu Glu Leu
130             135             140             145 tat cct gcc ttc ttt ggc tat tac ttc ttc aat tcc atg atg gga gtt         897
Tyr Pro Ala Phe Phe Gly Tyr Tyr Phe Phe Asn Ser Met Met Gly Val
                 150             155             160 cta cag ctg ctg cat atc ttc tgg gcc tac ctc att ttg cgc atg gcc         945
Leu Gln Leu Leu His Ile Phe Trp Ala Tyr Leu Ile Leu Arg Met Ala
             165             170             175 cac aag ttc ata act gga aag ctg gta gaa gat gaa cgc agt gac cgg         993
His Lys Phe Ile Thr Gly Lys Leu Val Glu Asp Glu Arg Ser Asp Arg
             180             185             190 gaa gaa aca gag agc tca gag ggg gag gag gct gca gct ggg gga gga         1041
Glu Glu Thr Glu Ser Ser Glu Gly Glu Glu Ala Ala Ala Gly Gly Gly
         195             200             205 gca aag agc cgg ccc cta gcc aat ggc cac ccc atc ctc aat aac aac         1089
Ala Lys Ser Arg Pro Leu Ala Asn Gly His Pro Ile Leu Asn Asn Asn
210             215             220             225 cat cgt aag aat gac tgaaccatta ttccagctgc ctcccagatt aatgcataaa          1144
His Arg Lys Asn Asp
                 230 gccaaggaac taccctgctc cctgcgctat agggtcactt taagctctgg ggaaaaagga       1204 gaaagtgaga ggagagttct ctgcatcctc cctccttgct tgtcacccag ttgcctttaa       1264 accaaattct aaccagccta tccccaggta gggggggacgt tggttatatt ctgttagagg      1324 gggacggtcg tattttcctc cctacccgcc aagtcatcct ttctactgct tttgaggccc       1384 tccctcagct ctctgtgggt aggggttaca attcgcattc cttattctga gaatttggcc      1444 ccagctgttt gcctttgact ccctgacctc cagagccagg gttgtgcctt attgtcccat      1504 ctgtgggcct cattctgcca aagctggacc aaggctaacc tttctaagct ccctaacttg      1564 ggccagaaac caaagctgag ctttaacctt tctccctcta tgacacaaat gaattgaggg     1624
```

```
taggaggagg gtgcacataa cccttaccct acctctgcca aaaagtgggg gctgtactgg    1684
ggactgctcg gatgatcttt cttagtgcta cttctttcag ctgtccctgt agcgacaggt    1744
ctaagatctg actgcctcct ttctctggcc tcttccccct tccctcttct cttcagctag    1804
gctagctggt ttggagtaga atggcaacta attctaattt ttatttatta aatatttggg    1864
gttttggttt taaagccaga attacggcta gcacctagca tttcagcaga gggaccattt    1924
tagaccaaaa tgtactgtta atgggttttt ttttaaaatt aaaagattaa ataaaaaata    1984
ttaaataaaa aaaaaaaaaa aaa                                            2007
```

US 7,037,683 B2

HUMAN LONGEVITY ASSURANCE PROTEIN, ITS CODING SEQUENCE AND THEIR USE

CROSS-REFERENCE TO RELATED APPLICATIONS

This application is a continuation of International Patent Application PCT/CN01/00105, filed on Jan. 31, 2001, which claims priority to Chinese Patent Application CN 00125197.X, filed on Sep. 14, 2000, the contents of which are herein incorporated in their entirety by reference.

FIELD OF INVENTION

This invention relates to the field of biotechnology, and, in particular, relates to a novel polynucleotide encoding human longevity assurance protein and the polypeptide encoded by said polynucleotide. The invention also relates to the uses and preparation of these polynucleotides and polypeptides.

TECHNICAL BACKGROUND

The division numbers of human and mammalian cells are fixed. After each division, the division potential in the progeny cells decreases. After a certain number of divisions, cells are not able to divide any more, become aged and start to apoptosis. Generally, it is considered that there are few exceptions in human except for testis spermatogonium. However, ⅔ of tumor cells are not limited to the above mechanism and have the potential of infinite division, indicating tumor cells have a mechanism for persistent division. The common recognition is that the division number of normal cell has something to do with the length of telomere in cell chromosome. After each division, the length of telomere is shortened once. After a certain number of divisions, telomere is shorten to a certain length and the cell stops division. But the tumor cells or reproductive cells have telomerase which repairs their telomere after each division, thus keeping the length of telomere. Therefore, it is believed now that the mammalian cells must depend on telomerase to keep the immortalization of cell.

However, the immortalization in yeast cells has a particular mechanism. As to the division of yeast cell, a single cell may have a fixed number of division, but its progeny cell maintains the division potential of the parental cell of division. Therefore, yeast cells as a population is immortalized. This mechanism does not depend on the length of telomere (D'mello N. P. and Jazwinski S. M, J. Bacteriol. 173: 7609–7613, 1991). The longevity assurance gene Lag1Sc in the yeast cell is involved in the mechanism which controls and guarantees yeast cell to keep the constant division number after the yeast cell divides (D'mello N. P., Childress D. S., Franklin S. P et al, J. Biol. Chem, 269: 15451–15459, 1994).

In 1998, Jiang et al. isolated a related human gene Lag1Hs from human somatic gene library that was homologous to yeast Lag1 (Jiang J. C. Kirchman P. A. Zagulski M etc., Genome Res. 8: (12) 1259–1272, 1998. GenBank Nos. AF 105005–AF 105009). As to the function, Lag1Hs could rescue the Lag1 Δ/Lac1 Δ double deficient yeast strain from death and recover its ability of division. The above authors found that said gene was expressed in body brain and muscle tissue, and considered that the above gene might relate to degenerative disorders of human nerve.

Therefore, it is of great importance to study and develop human longevity assurance gene and protein for the purpose of therapy.

Since cancer is one of the main diseases harmful to human health, people are concerned about the gene therapy of cancer so as to effectively cure and prevent tumors. Therefore, there is a keen need in the art to develop new tumor-inhibiting human proteins and their agonist/antagonist.

SUMMARY OF INVENTION

One purpose of the invention is to provide a novel longevity assurance protein, which was named LAG1 Hs2 protein and is recently named LASS2 protein, and its fragments, analogs and derivatives.

Another purpose of the invention is to provide a polynucleotide encoding said polypeptides.

Still another purpose of the invention is to provide a method for preparing said polypeptides and the uses of said polypeptides and their encoding sequences.

In the first aspect, the invention provides an isolated LASS2 polypeptide, which comprises a polypeptide having the amino acid sequence of SEQ ID NO: 2, its conservative variants, its active fragments, and its active derivatives.

Preferably, said polypeptide is a polypeptide having the amino acid sequence of SEQ ID NO: 2.

In the second aspect, the invention provides an isolated polynucleotide, which comprises a nucleotide sequence sharing at least 85% homology to the following nucleotide sequence: (a) the nucleotide sequence encoding the above LASS2 polypeptide; (b) the polynucleotide complementary to nucleotide sequence of (a). Preferably; said nucleotide sequence encodes a polypeptide comprising the amino acid sequence of SEQ ID NO: 2. More preferably, said polynucleotide comprises the ORF sequence or full-length sequence of SEQ ID NO: 3.

In the third aspect, the invention provides a vector comprising the above polynucleotide, and a host cell transformed with said vector or a host cell transformed with said polynucleotide.

In the fourth aspect, the invention provides a method for producing a polypeptide having the activity of LASS2 protein, which comprises:
(a) culturing the above transformed host cell under the conditions suitable for the expression of protein;
(b) isolating the polypeptides having the activity of LASS2 protein from the culture.

In the fifth aspect, the invention provides an antibody specifically bound to LASS2 protein. Also provided are nucleic acid molecules comprising consecutive 10–800 nucleotides of the above polynucleotide.

In the sixth aspect, the invention provides pharmaceutical composition comprising a safe and efficient amount of hepatocarcinoma associated LASS2 protein and pharmaceutically acceptable carrier. Said pharmaceutical composition can be used for the therapy of diseases, such as cancer and cell abnormal proliferation.

The other aspects of the invention will be apparent to the skilled in the art in light of the technical disclosure of the invention.

DESCRIPTION OF THE DRAWINGS

Lane 1: blank control; Lane 2: PinPoint™ DNA control which encodes CAT fusion protein of about 39 kDa; Lane 3: pT7X-LAG1 Hs 2 (about 27 kDa); Lane 4: pT7Zza–LAG1 Hs 2 (Zza+Sp260 fusion protein, about 41 kDa).

DETAILED DESCRIPTION OF INVENTION

In the present invention, the cDNA clones were transformed into cancer cells in a large scale. On the basis of tumor-inhibiting results, the genes were sequenced to confirm their novelty. Further, the full-length cDNA were obtained and DNA transformation experiments were carried out. The human longevity assurance protein of the invention, i.e., LAG1 Hs 2, was proved to inhibit the formation of clones of cancer cell, e.g., hepatocarcinoma cell.

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, the terms "isolated LAG1 Hs2 protein or polypeptide" mean that LAG1 Hs2 polypeptide does not essentially contain other proteins, lipids, carbohydrate or any other substances associated therewith in nature. The skilled in the art can purify LAG1 Hs2 protein by standard protein purification techniques. Essentially purified polypeptide forms a single main band on a non-reductive PAGE gel. The purity of LAG1 Hs2 polypeptide can be analyzed by amino acid sequence analysis.

The polypeptide of invention may be a recombinant polypeptide, natural polypeptide, or synthetic polypeptide, preferably a recombinant polypeptide. The polypeptide of invention may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the protocol of recombinant production, the polypeptide of invention may be glycosylated or non-glycosylated. The polypeptide of invention may or may not comprise the starting Met residue.

The invention further comprises the fragments, derivatives and analogues of LAG1 Hs2. As used in the invention, the terms "fragment", "derivative" and "analogue" mean the polypeptide that essentially retains the same biological functions or activity of LAG1 Hs2 protein of the invention. The fragment, derivative or analogue of the polypeptide of invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretary sequence or a sequence which is employed for purification of the mature polypeptide or a proprotein sequence, e.g., a fusion protein formed with IgC fragment. Such fragments, derivatives and analogs are deemed to be within the scope of those skilled in the art from the teachings herein.

In the present invention, the term "human LAG1 Hs2 polypeptide" or "LAG1 Hs2 protein" refers to a polypeptide having the activity of human LAG1 Hs2 protein comprising the amino acid sequence of SEQ ID NO: 2. The term also comprises the variants of said amino acid sequence which have the same function of human LAG1 Hs2. These variants include, but are not limited to, deletions, insertions and/or substitutions of several amino acids (typically 1–50, preferably 1–30, more preferably 1–20, most preferably 1–10), and addition of one or more amino acids (typically less than 20, preferably less than 10, more preferably less than 5) at C-terminal and/or N-terminal. For example, the protein functions are usually unchanged when an amino residue is substituted by a similar or analogous one. Further, the addition of one or several amino acids at C-terminal and/or N-terminal will not change the function of protein. The term also includes the active fragments, and derivatives of LAG1 Hs2 protein.

The variants of polypeptide include homologous sequences, allelic variants, natural mutants, induced mutants, proteins encoded by DNA which hybridizes to LAG1 Hs2 DNA under high or low stringency conditions as well as the polypeptides or proteins retrieved by antisera raised against LAG1 Hs2 polypeptide. The present invention also provides other polypeptides, e.g., fusion proteins, which include the LAG1 Hs2 polypeptide or fragments thereof. In addition to substantially full-length polypeptide, the soluble fragments of LAG1 Hs2 polypeptide are also included. Generally, these fragments comprise at least 10, typically at least 30, preferably at least 50, more preferably at least 80, most preferably at least 100 consecutive amino acids of LAG1 Hs2 polypeptide.

The present invention also provides the analogues of LAG1 Hs2 protein or polypeptide. Analogues can differ from naturally occurring LAG1 Hs2 polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

In the invention, "LAG1 Hs2 conservative mutant" means a polypeptide formed by substituting at most 10, preferably at most 8, more preferably 5, and most preferably at most 3 amino acids with the amino acids having substantially the same or similar property, as compared with the amino acid sequence of SEQ ID NO: 2. Preferably, these conservative mutants are formed by the substitution according to Table 1.

TABLE 1

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Giy (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The polynucleotide according to the invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NO: 3, or is a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 3.

The sequences encoding the mature polypeptide of SEQ ID NO: 2 include those encoding only the mature polypeptide, those encoding mature polypeptide plus various additional encoding sequence, the encoding sequence for mature polypeptide plus the non-encoding sequence and optional additional encoding sequence.

The term "polynucleotide encoding the polypeptide" includes the polynucleotide encoding said polypeptide and the polynucleotide comprising additional and/or non-encoding sequence.

The invention further relates to the variants of the hereinabove polynucleotides which encode a polypeptide having the same amino acid sequence of invention, or its fragment, analogue and derivative. The variant of the polynucleotide may be a naturally occurring allelic variant of the polynucleotide or a non-naturally occurring variant of the polynucleotide. Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The present invention further relates to polynucleotides, which hybridize to the hereinabove-described sequences, if there is at least 50%, preferably at least 70%, more preferably at least 80%, and most preferably at least 90% identity between the sequences. The present invention particularly relates to polynucleotides, which hybridize under stringent conditions to the polynucleotides of the invention. As herein used, the term "stringent conditions" means the following conditions: (1) hybridization and washing under low ionic strength and high temperature, such as 0.2×SSC, 0.1% SDS, 60° C.; (2) hybridization after adding denaturants, such as 50% (v/v) formamide, 0.1% bovine serum/0.1% Ficoll, 42° C.; or (3) hybridization of two sequences sharing at least 95%, preferably 97% homology. Further, the polynucleotides which hybridize to the hereinabove described polynucleotides encode a polypeptide which retains the same biological function or activity as the mature polypeptide as set forth in SEQ ID NO: 2

The invention also relates to nucleic acid fragments hybridized with the hereinabove sequence. As used in the present invention, the length of the "nucleic acid fragment" is at least 15 bp, preferably at least 30 bp, more preferably at least 50 bp, and most preferably at least 100 bp. The nucleic acid fragment can be used in the amplification techniques of nucleic acid, e.g., PCR, so as to determine and/or isolate the polynucleotide encoding human longevity assurance protein.

The polypeptide and polynucleotide of the invention are preferably in isolated form, preferably purified to be homogenous.

According to the invention, the DNA sequence can be obtained in various ways. For example, the polynucleotide is isolated by the hybridization techniques well-known in the art, which includes, but are not limited to 1) the hybridization between the probe and genomic or cDNA library so as to select the homologous polynucleotide sequence, and 2) expression of the antibodies against the library so as to screen out the DNA fragments having the common structure features.

The specific DNA fragment sequences encoding human longevity assurance protein may further be obtained by the following methods so as to obtain the double-stranded DNA for said polypeptide: 1) isolating double-stranded DNA sequence from genomic DNA; and 2) chemical synthesis of DNA sequence.

In the above methods, the isolation of genornic DNA is least frequently used. The direct chemical synthesis of DNA sequence is commonly used when the whole amino acid sequence of the desired polypeptide product is known. When the whole amino acid sequence of the desired polypeptide product is not known, the direct chemical synthesis of DNA sequence is impossible and the method is to isolate cDNA sequence. The standard method for isolating the cDNA of interest is to isolate mRNA from donor cells that highly express said gene followed by reverse transcription of mRNA to form plasmid or phage cDNA library. There are many sophisticated techniques for extracting mRNA and the kits are commercially available (QIAGEN™). The conventional method can be used to construct cDNA library (Sambrook, et al., Molecular Cloning, A Laboratory Manual, Cold Spring Harbor Laboratory. New York, 1989). The cDNA libraries are also commercially available, e.g., the different cDNA library from CLONTECH™. When PCR is used in combination, even an extremely small amount of expression products can be cloned.

The conventional methods can be used for screening the gene of invention from a library. These methods include, but are not limited to, (1) DNA-DNA or DNA-RNA hybridization, (2) the appearance or loss of the function of marker gene, (3) the determination of the level of LAG1 Hs2 transcripts, (4) the determination of protein product of gene by immunology methods or the biological activity assays. These methods can be used alone or in combination.

In method (1), the probe used in the hybridization could be identical to any portion of polynucleotide of invention.

The length of probe is typically at least 15, preferably at least 30, more preferably at least 50, and most preferably at least about 100 nucleotides. Usually, the length of probe is less than 2 kb, preferably 1 kb. The probe usually is the DNA sequence chemically synthesized on the basis of the sequence information of gene of invention. Of course, the gene of invention itself or the fragment thereof can be used as a probe. The labels for DNA probe include, e.g., radioactive isotopes, fluoresceins or enzymes, such as alkaline phosphatase.

In method (4), the detection of the protein products expressed by LAG1 Hs2 gene can be carried out by immunology methods, such as Western blotting, radioimmunoassay, and ELISA.

The method of amplification of DNA/RNA by PCR (Saiki, et al. Science 1985; 230:1350–1354) is preferably used to obtain the gene of the invention. Especially when it is difficult to obtain the full-length cDNA, the method of RACE is preferably used. The primers used in PCR can be properly selected according to the polynucleotide sequence information of invention disclosed herein and synthesized by the conventional methods. The amplified DNA/RNA fragments can be isolated and purified by conventional methods such as gel electrophoresis.

For the gene of the invention or its DNA fragments, the sequencing of polynucleotide sequence can be carried out by the conventional dideoxy sequencing method (Sanger et al. PNAS, 1977, 74: 5463–5467). The sequencing of polynucleotide sequence can also be carried out using the commercially available sequencing kits. In order to obtain the full-length cDNA sequence, it is necessary to repeat the sequencing. Sometimes, it may sequence the DNA of several clones to obtain the full-length cDNA sequence.

The invention further relates to a vector comprising the polynucleotide of the invention, a genetic engineered host cell transformed with the vector of the invention or directly with the sequence encoding LAG1 Hs2 protein, and the method for producing the polypeptide of invention by recombinant techniques.

The recombinant human LAG1 Hs2 polypeptides can be expressed or produced by the conventional recombinant DNA technology (Science, 1984; 224:1431), using the polynucleotide sequence of invention. Generally, it comprises the following steps:

(1) transfecting or transforming the appropriate host cells with the polynucleotide encoding LAG1 Hs2 polypeptide of the invention or the vector containing said polynucleotide;

(2) culturing the host cells in an appropriate medium;

(3) isolating or purifying the protein from the medium or cells.

In the present invention, the polynucleotide sequences encoding human longevity assurance protein may be inserted into a recombinant expression vector. The term "expression vector" refers to a bacterial plasmid, bacteriophage, yeast plasmid, plant virus or mammalian cell virus, such as adenovirus, retrovirus or any other vehicle known in the art. Vectors suitable for use in the present invention include, but are not limited to, the T7-based expression vector for expression in bacteria (Rosenberg, et al., Gene, 56:125, 1987), the pMSXND expression vector for expression in mammalian cells (Lee and Nathans, J Biol. Chem., 263:3521, 1988) and baculovirus-derived vectors for expression in insect cells. On the whole, any plasmid or vector can be used to construct the recombinant expression vector as long as it can replicate and is stable in the host. One important feature of expression vector is that the expression vector typically contains an origin of replication, a promoter, a marker gene as well as the translation regulatory components.

The methods known by the artisans in the art can be used to construct an expression vector containing the DNA sequence of LAG1 Hs2 and appropriate transcription/translation regulatory components. These methods include in vitro recombinant DNA technique, DNA synthesis technique, in vivo recombinant technique and so on (Sambrook, et al. Molecular Cloning, a Laboratory Manual, Cold Spring Harbor Laboratory. New York, 1989). The DNA sequence is efficiently linked to the proper promoter in an expression vector to direct the synthesis of mRNA. The exemplary promoters are lac or trp promoter of E. coli; $P_L$ promoter of λ phage; eukaryotic promoter including CMV immediate early promoter, HSV thymidine kinase promoter, early and late SV40 promoter, LTRs of retrovirus and some other known promoters which control the gene expression in the prokaryotic cells, eukaryotic cells or virus. The expression vector may further comprise a ribosome-binding site for initiating the translation, transcription terminator and the like.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for E. coli.

The vector containing said DNA sequence and proper promoter or regulatory elements can be transformed into appropriate host cells to express the protein.

The "host cell" includes prokaryote, such as bacteria; primary eukaryote, such as yeast; advanced eukaryotic, such as mammalian cells. The representative examples are bacterial cells, such as E. coli, Streptomyces, Salmonella typhimurium; fungal cells, such as yeast; plant cells; insect cells such as Drosophila S2 or Sf9; animal cells such as CHO, COS or Bowes melanoma, etc.

Transcription of the polynucleotide of invention in higher eukaryotes is increased by inserting an enhancer sequence into the vector. Enhancers are cis-acting elements of DNA, usually about from 10 to 300 bp that act on a promoter to increase the gene transcription. Examples include the SV40 enhancer on the late side of the replication origin 100 to 270 bp, the polyoma enhancer on the late side of the replication origin, and adenovirus enhancers.

The skilled in the art know clearly how to select appropriate vectors, promoters, enhancers and host cells.

Recombinant transformation of host cell with the DNA sequence of invention might be carried out by conventional techniques well known to those skilled in the art. Where the host is prokaryotic such as E. coli, the competent cells, which are capable of DNA uptake, can be prepared from cells harvested after exponential growth phase and subsequently treated by the $CaCl_2$ method using procedures well known in the art. Alternatively, $MgCl_2$ can be used. The transformation can also be carried out by electroporation, if desired. When the host is an eukaryote, such methods of transfection of DNA as calcium phosphate co-precipitates, conventional mechanical procedures such as microinjection, electroporation, or liposome-mediated transfection may be used.

The transformants are cultured using conventional methods to express the polypeptides of the invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to conventional renaturation treatment, treatment by protein precipitant (such as salt precipitation), centrifugation, cell lysis by osmosis, sonication, supercentrifugation, molecular sieve chromatography or gel chromatography, adsorption chromatography, ion exchange chromatagraphy, HPLC, and any other liquid chromatagraphy, and the combination thereof.

Therefore, the recombinant human LAG1 Hs2 protein or polypeptide have various uses including, but not to be limited to: curing disorders caused by low or no activity of LAG1 Hs2 protein (e.g., inhibiting the growth of tumor), and screening out antibodies, polypeptides or ligands as agonists or antagonists of LAG1 Hs2. For example, antibodies can be used to activate or inhibit the function of LAG1 Hs2 protein. The expressed recombinant LAG1 Hs2 protein can be used to screen polypeptide library to find out therapeutically valuable polypeptide molecules which inhibit or activate LAG1 Hs2 protein.

The invention also provides the method for screening compounds so as to identify agents which improve LAG1 Hs2 protein (agonists) or repress LAG1 Hs2 protein (antagonists). For example, in the presence of an agent, the mammal cells or the membrane preparation expressing LAG1 Hs2 protein can be incubated with the labeled LAG1 Hs2 protein to determine the ability of the agent to enhance or repress the interaction.

The antagonists of LAG1 Hs2 protein include the screened antibodies, compounds, receptor deletants and analogues. The antagonists of LAG1 Hs2 protein can bind to LAG1 Hs2 protein and eliminate its function, or inhibit the production of LAG1 Hs2, or bind to the active site of said polypeptide so that the polypeptide can not function biologically. The antagonists of LAG1 Hs2 protein can be used in the therapy.

When screening the compound as an antagonist, LAG1 Hs2 protein may be added into the biological assay. One can determine whether the compound is an antagonist by determining the its effect on the interaction between LAG1 Hs2 protein and its receptor. Using the method same as that for screening compounds, one can screen out the receptor deletants and analogues acting as antagonists.

The polypeptide of invention can be directly used for the treatment of diseases, e.g., various malignant tumors, abnormal cell proliferation.

The polypeptide, and its fragment, derivative, analogue or cells can be used as antigens to produce antibodies. These antibodies may be polyclonal or monoclonal antibodies. The polyclonal antibodies can be prepared by immunizing animals with LAG1 Hs2 protein. The techniques for producing monoclonal antibodies against LAG1 Hs2 protein include, but are not limited to, the hybridoma technique, the trioma technique, the human B-cell hybridoma technique, the EBV-hybridoma technique and so on.

According to the invention, the polypeptides, and its antagonists may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient which does not influence the effect of the drug. These compositions can be used for treatment of disease.

The invention also provides a pharmaceutical pack or kit comprising one or more containers filled with one or more of the ingredients of the pharmaceutical compositions of the invention. Associated with such container (s) can be a notice in the form prescribed by a governmental agency regulating the manufacture, use or sale of pharmaceuticals or biological products, which notice reflects approval by the agency of manufacture, use or sale for human administration. In addition, the polypeptides of the invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The LAG1 Hs2 protein is administered in an amount, which is effective for treating and/or prophylaxis of the specific indication. The amount of LAG1 Hs2 protein administrated on patient will depend upon various factors, such as delivery methods, the subject health, and the like, and is within the judgment of the skilled clinician.

LAG1 Hs2 polynucleotides also have many therapeutic applications. Gene therapy technology can be used in the therapy of the abnormal cell proliferation, development or metabolism, which is caused by the loss of LAG1 Hs2 expression or the expression of abnormal or non-active LAG1 Hs2. Recombinant gene therapy vectors, such as virus vectors, can be designed to express mutated LAG1 Hs2 so as to inhibit the activity of endogenous LAG1 Hs2. One form of the-mutated LAG1 Hs2 is a truncated LAG1 Hs2 whose signal transduction domain is deleted. Therefore, this mutated LAG1 Hs2 can bind the downstream substrate without the activity of signal transduction. Thus, the recombinant gene therapy vectors can be used to cure the diseases caused by the abnormal expression or activity of LAG1 Hs2. The expression vectors derived from virus, such as retrovirus, adenovirus, adeno-associated virus, herpes simplex virus, parvovirus, and so on, can be used to introduce the LAG1 Hs2 gene into the cells. The methods for constructing a recombinant virus vector harboring LAG1 Hs2 gene are described in the literature (Sambrook, et al.). In addition, the recombinant LAG1 Hs2 gene can be packed into liposome and then transferred into the cells.

Also included in the invention are ribozyme and the oligonucleotides, including antisense RNA and DNA, which inhibit the translation of LAG1 Hs2 mRNA. Ribozyme is an enzyme-like molecule capable of specifically cutting certain RNA. The mechanism is the nucleic acid endo-cleavage after the specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and in the downstream of RNA polymerase promoter. In order to increase stability, the nucleic acid molecules can be modified in many manners, e.g., increasing the length of the flanking sequences, replacing the phosphodiester bond with the phosphothioester bond in the oligonucleotide.

The methods for introducing the polynucleotides into tissues or cells include: directly injecting the polynucleotides into tissue in the body, in vitro introducing the polynucleotides into cells with vectors, such as virus, phage, or plasmid, and then transplanting the cells into the body.

The polypeptide of invention is useful in the analysis of peptide spectrum. For example, the polypeptide can be specifically cut by physical, chemical, or enzymatic means, and then analyzed by one, two or three dimensional gel electrophoresis.

The invention also provides the antibodies against the determinants of LAG1 Hs2 protein. These antibodies include, but are not limited to, polyclonal antibody, monoclonal antibody, chimeric antibody, single-chain antibody, Fab fragment and the fragments produced by Fab expression library.

The antibody against LAG1 Hs2 protein can be used in immunohistochemical method to detect the presence of LAG1 Hs2 protein in the biopsy specimen.

The monoclonal antibody specific to LAG1 Hs2 protein can be labeled by radioactive isotopes, and injected into human body to trace the location and distribution of LAG1 Hs2 protein. This radioactively labeled antibody can be used in the non-wounding diagnostic method for the mapping of the tumor and determination of the metastasis of tumor cells.

The antibody of the invention is useful for the therapy or the prophylaxis of disorders related to the LAG1 Hs2 protein. The appropriate amount of antibody can be administrated to stimulate or block the production or activity of LAG1 Hs2 protein.

Antibodies can also be designed as an immunotoxin targeting at the particular site in the body. For example, a monoclonal antibody having high affinity to LAG1 Hs2 protein can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill LAG1 Hs2 protein-positive cells.

The polyclonal antibodies can be prepared by immunizing animals, such as rabbit, mouse, and rat, with LAG1 Hs2 protein. Various adjuvants, e.g., Freund's adjuvant, can be used to enhance the immunization.

The techniques for producing LAG1 Hs2 protein monoclonal antibodies include the hybridoma technique (Kohler and Milstein. Nature, 1975, 256:495–497). The chimeric antibody comprising a constant region of human origin and a variable region of non-human origin can be produced using the conventional method in the art (Morrison et al, PNAS, 1985, 81:6851). Furthermore, the techniques for producing single-chain antibody (U.S. Pat. No. 4,946,778) are also useful for preparing the single-chain antibody against LAG1 Hs2 protein.

The polypeptide molecule capable of binding to LAG1 Hs2 protein can be obtained by screening out the random polypeptide library consisting of the various combinations of amino acids bound onto the solid matrix. Typically, LAG1 Hs2 protein is labeled in the screening.

The invention further provides diagnostic assays for quantitative and in situ measurement of LAG1 Hs2 protein level. These assays are well known in the art and include FISH assay and radioimmunoassay. The level of LAG1 Hs2 protein detected in the assay can be used to illustrate the importance of LAG1 Hs2 protein in diseases and to determine the diseases associated with LAG1 Hs2 protein.

The polynucleotide encoding LAG1 Hs2 protein can be used in the diagnosis of LAG1 Hs2 protein related diseases. The polynucleotide encoding LAG1 Hs2 can be used to detect whether LAG1 Hs2 is expressed or not, and whether the expression of LAG1 Hs2 is normal or abnormal, e.g., in the case of diseases. LAG1 Hs2 DNA sequences can be used in the hybridization with biopsy samples to determine the expression of LAG1 Hs2. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analysis the differential expression of genes in tissues and for the diagnosis of genes. The LAG1 Hs2 specific primers can be used in RNA-polymerase chain reaction and in vitro amplification to detect the transcripts of LAG1 Hs2.

Further, detection of the mutation of LAG1 Hs2 gene is useful for the diagnosis of LAG1 Hs2 protein related diseases. The mutation forms of LAG1 Hs2 include site mutation, translocation, deletion, rearrangement and any other mutations compared with the wild-type LAG1 Hs2 DNA sequence. The conventional methods, such as Southern blotting, DNA sequencing, PCR and in situ blotting, can be used to detect mutation. Moreover, mutation sometimes affects the expression of protein. Therefore, Northern blotting and Western blotting can be used to indirectly determine whether the gene is mutated or not.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In brief, sequences can be mapped to chromosomes by preparing PCR primers (preferably 15–35 bp) from the cDNA. These primers are then used for PCR screening of somatic cell hybrids containing individual human chromosomes. Only the cell hybrids, which contain the genes corresponding to the primers, produce amplified fragments.

The PCR mapping by using somatic cell hybrids is a rapid method to map a DNA to its chromosome. Using the oligonucleotide primers of the invention and similar methods, one can use a group of fragments from a particular chromosome or a lot of genomic clones to achieve the sub-location. Other mapping strategies that can similarly be used to map a sequence to its chromosome include in situ hybridization, pre-screening with labeled flow-sorted chromosomes, and pre-selection by hybridization to chromosome specific cDNA libraries.

For example, the accurate chromosome mapping can be performed by hybridizing cDNA clones to a chromosome in metaphase using FISH technique. For details, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found in, e.g., Mendelian Inheritance in Man (available on-line through Johns Hopkins University Welch Medical Library). The relationships between genes and diseases that have been mapped to the same chromosomal region are then identified through linkage analysis.

Then, the differences in the cDNA or genomic sequence between affected and unaffected individuals can also be determined. If a mutation is observed in some or all of the affected individuals but not in any normal individual, then the mutation is likely to be the causative agent of the disease. Comparison of affected and unaffected individuals generally involves first looking for structural alterations in the chromosomes, such as deletions or translocations that are visible from chromosome spreads or detectable using PCR based on that cDNA sequence. According to the present resolving ability of physical mapping and gene mapping, the cDNA accurately located to a disease related chromosome region might be one of 50–500 potential disease genes (it is presumed that the mapping resolving ability is 1 mega bases and one gene corresponds to 20 kb bases)

The full length LAG1 Hs2 nucleotide sequence or its fragment of the invention can be prepared by PCR amplification, recombinant method and synthetic method. For PCR amplification, one can obtain said sequences by designing primers based on the nucleotide sequence disclosed in the invention, especially the sequence of ORF, and using cDNA library commercially available or prepared by routine techniques known in the art as a template. When the sequence is long, it is usually necessary to perform two or more PCR amplifications and link the amplified fragments together in the correct order.

Once the sequence is obtained, a great amount of the sequences can be produced by recombinant methods. Usually, said sequence is cloned in a vector which is then transformed into a host cell. Then the sequence is isolated from the amplified host cells using conventional techniques.

Further, the sequence can be produced by synthesis, especially when the fragment is short. Typically, several small fragments are synthesized and linked together to obtain a long sequence.

At present, it is completely feasible to chemically synthesize the DNA sequence encoding the protein of the invention, or the fragments or derivatives thereof. In addition, the mutation can be introduced into the sequence of the protein by chemical synthesis.

In one embodiment of the invention, a clone was isolated from human liver cDNA library. Said clone shared 44% (83/183) homology in amino acid sequence with yeast Lag1 and entitled LAG1 Hs 2. Further, said clone shared 46% (89/191) homology in amino acid sequence with human related gene LAG1 Hs reported by Jiang and had the common Lag1P motif in human and yeast. Therefore, based on the bio-informatics, it was confirmed that the new LAG1 Hs 2 was a new human gene homologous to yeast LAG1, and entitled "human longevity assurance gene". As to the function, it has been found that LAG1 Hs 2 can in vitro inhibit the growth of hepatocarcinoma cell, and in vivo inhibit the growth of tumor in nude mice. Further, Northern hybridization indicated that LAG1 Hs 2 gene of the invention had high level of mRNA expression in kidney, liver tissue, low expression in brain, heart, placenta, and lung, and no expression in muscle, colon, thymus gland, spleen, small intestine, and peripheral leukocyte. In situ hybridization results indicated that, compared with hepatocarcinoma tissue, the expression of LAG1 Hs2 in normal liver was higher than that in the noncancerous liver tissue, and the expression of LAG1 Hs2 in noncancerous liver tissue was higher than that in the cancerous liver tissue. Therefore, the expression of said gene was proved to be down-regulated in human hepatocarcinoma.

Because LAG1 Hs 2 inhibits the growth of tumor cells, it has not only the function of regulating cell division but also the potential value in the treatment and diagnosis of malignant tumor. Since the LAG1 Hs2 protein of the invention has the natural amino acid sequence from human, it is predicted that, compared with the other proteins in the same family from other animals, it has higher activity and/or lower side-effect when administrated to human. For example, there is no or low immunogenicity in vivo.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Isolation of LAG1 Hs 2 cDNA Clone and its Inhibitory Effect on the Growth of Human Hepatocarcinoma Cell The human liver cDNA library (Catalog. 10422-012) was bought from GIBCO BRL Company. In the first round, the cDNA clones were randomly selected. Then the cDNA clones which were highly abundant or which were proved to exhibit tumor inhibiting function were used as probes to hybridize and screen the cDNA library. The weakly positive and negative clones were picked up. The plasmid DNAs were extracted using QIAGEN™ 96-well plate plasmid Extraction Kit according to the specification of the manufacturer. Plasmid DNA and blank vector were used to transform hepatocarcinoma cell line 7721. After 100ng DNA was precipitated by ethanol and dried, 6 μl $H_2O$ was added to solve DNA for transfection. To each DNA sample, 0.74 μl liposome and 9.3 μl serum-free medium were added, mixed, and placed at room temperature for 10 min. Into each tube, 150 μl serum-free medium was added. Then the mixture was divided into three parts and added into 3 wells of 96-well plate in which 7721 cells were kept growing at 37° C. for 2 hours. Additional 50 μl serum-free medium was added into each well and placed at 37° C. for 24 hours. In each well, the medium was replaced by 100 μl complete culture medium. After placed at 37° C. for 24 hours, it was replaced by 100 μl complete culture medium containing G418. After 37° C. for 24–48 hours, we replaced the medium with culture medium containing different concentration of G4 18 and observed results. After about 2–3 times, clones were formed in the microscopy and counted. The results indicated that SP260 cDNA clone exhibited the ability to inhibit the formation of clones (The numbers of formed clones for blank vector were 38, 40, and 42, while for SP260 cDNA clone, the numbers were 1, 7, and 17).

For cDNA clone SP260, about 500 bp nucleotide sequence at one end was sequenced on ABI377 DNA automatic sequencer using dideoxy termination method. On analysis, it was determined to be a new gene clone. After sequencing the other end of the SP260, the full length cDNA was not yet obtained. The primers were designed and the sequencing was repeated until the full length sequence was obtained.

The sequence analysis of SP260 cDNA clone indicates that the gene was incomplete. So the SMART RACE cDNA Amplification Kit (Cat. No. K1811-1, CLONTECH™, Inc.), and specific primers of 5' GGAAGGGGGAAGAGG CCAGAGAAAG 3' and 5'. TCCCAGTACAGCCCCCACTTTTTG 3' were used. After operating according to the specification, the full length clone was obtained and named LAG 1 Hs2. Said gene was recently named as LASS2 (longevity assurance homolog 2) by HUGO.

EXAMPLE 2

Sequence Analysis of LAG1 Hs 2 cDNA

The full length cDNA prepared in Example 1 was 2007 bp, contained a 690 bp ORF (position 415-1105) and encoded a protein consisting of 230 amino acids (the stop codon was not included).

```
A: Nuclotide sequence: length: 2007 bp
     1 CTAGAATTCA GCGGCCGCTG AATTCTAGAA GCCGATCTAG AAGACCGAGA (SEQ ID NO: 1)

51 TGGACGTGTC TACGCCAAAG CCTCAGATCT CTATATCACG CTGGCCCTGG

101 CCTTGCTCTT CCTCATCGTT CGATACTTCT TTGAGGTGTA CGTGGCTACA

151 CCACTGGCTG CCCTCTTGAA CATAAAGGAG AAAACTCGGC TGCGGGCACC

201 TCCCAACGCC ACCTTGGAAC ATTTCTACCT GACCAGTGGC AAGCAGCCCA

251 AGCAGGTGGA AGTAGAGCTT TTGTCCCGGC AGAGCGGGCT CTCTGGCCGC

301 CAGGTAGAGC GTTGGTTCCG TCGCCGCCGC AACCAGGACC GGCCCAGTCT

351 CCTCAAGAAG TTCCGAGAAG CCAGCTGGAG ATTCACATTT TACCTGATTG

401 CCTTCATTGC CGGCATGGCC GTCATTGTGG ATAAACCCTG GTTCTATGAC

451 ATGAAGAAAG TTTGGGAGGG ATATCCCATA CAGAGCACTA TCCCTTCCCA

501 GTATTGGTAC TACATGATTG AACTTTCCTT CTACTGGTCC CTGCTCTTCA

551 GCATTGCCTC TGATGTCAAG CGAAAGGATT TCAAGGAACA GATCATCCAC

601 CATGTGGCCA CCATCATTCT CATCAGCTTT TCCTGGTTTG CCAATTACAT

651 CCGAGCTGGG ACTCTAATCA TGGCTCTGCA TGACTCTTCC GATTACCTGC

701 TGGAGTCAGC CAAGATGTTT AACTACGCGG GATGGAAGAA CACCTGCAAC

751 AACATCTTCA TCGTCTTCGC CATTGTTTTT ATCATCACCC GAGTGGTCAT

801 CCTGCCCTTG TGGATCCTGC ATTGCACCCT GGTGTAGCCA CTGGAGCTCT

851 ATCCTGCCTT CTTTGGCTAT TACTTCTTCA ATTCCATGAT GGGAGTTCTA

901 CAGCTGCTGC ATATCTTCTG GGCCTACCTC ATTTTGCGCA TGGCCCACAA

951 GTTCATAACT GGAAAGCTGG TAGAAGATGA ACGCAGTGAC CGGGAAGAAA

1001 CAGAGAGCTC AGAGGGGGAG GAGGCTGCAG CTGGGGGAGG AGCAAAGAGC

1051 GGGCCCCTAG CCAATGGCCA CCCCATCCTC AATAACAACC ATCGTAAGAA

1101 TGACTGAACC ATTATTCCAG CTGCCTCCCA GATTAATGCA TAAAGCCAAG

1151 GAACTACCCT GCTCCCTGCG CTATAGGGTC ACTTTAAGCT CTGGGGAAAA

1201 AGGAGAAAGT GAGAGGAGAG TTCTCTGCAT CCTCCCTCCT TGCTTGTCAC

1251 CCAGTTGCCT TTAAACCAAA TTCTAACCAG CCTATCCCCA GGTAGGGGGG

1301 ACGTTGGTTA TATTCTGTTA GAGGGGGACG GTCGTATTTT CCTCCCTACC

1351 CGCCAAGTCA TCCTTTCTAC TGCTTTTGAG GCCCTCCCTC AGCTCTCTGT

1401 GGGTAGGGGT TACAATTCGC ATTCCTTATT CTGAGAATTT GGCCCCAGCT

1451 GTTTGCCTTT GACTCCCTGA CCTCCAGAGC CAGGGTTGTG CCTTATTGTC

1501 CCATCTGTGG GCCTCATTCT GCCAAAGCTG GACCAAGGCT AACCTTTCTA

1551 AGCTCCCTAA CTTGGGCCAG AAACCAAAGC TGAGCTTTTA ACTTTCTCCC

1601 TCTATGACAC AAATGAATTG AGGGTAGGAG GAGGGTGCAC ATAACCCTTA

1651 CCCTACCTCT GCCAAAAAGT GGGGGCTGTA CTGGGGACTG CTCGGATGAT

1701 CTTTCTTAGT GCTACTTCTT TCAGCTGTCC CTGTAGCGAC AGGTCTAAGA
```

-continued
```
1751 TCTGACTGCC TCCTTTCTCT GGCCTCTTCC CCCTTCCCTC TTCTCTTCAG

1801 CTAGGCTAGC TGGTTTGGAG TAGAATGGCA ACTAATTCTA ATTTTTATTT

1851 ATTAAATATT TGGGGTTTTG GTTTTAAAGC CAGAATTACG GCTAGCACCT

1901 AGCATTTCAG CAGAGGGACC ATTTTAGACC AAAATGTACT GTTAATGGGT

1951 TTTTTTTTAA AATTAAAAGA TTAAATAAAA AATATTAAAT AAAAAAAAAA

2001 AAAAAAA
```

B: Amino acid sequence: length: 230 amino acids
```
  1 MAVIVDKPWF YDMKKVWEGY PIQSTIPSQY WYYMIELSFY WSLLFSIASD (SEQ ID NO: 2)

51 VKRKDFKEQI IHHVATIILI SFSWFANYIR AGTLIMALHD SSDYLLESAK

101 MFNYAGWKNT CNNIFIVFAI VFIITRLVIL PFWILHCTLV YPLELYPAFF

151 GYYFFNSMMG VLQLLHIFWA YLILRMAHKF ITGKLVEDER SDREETESSE

201 GEEAAAGGGA KSRPLANGHP ILNNNHRKND
```

C: Name of clone: (LAG 1 Hs 2 (SEQ ID NO: 3)
Starting codon: 415 ATG Stop codon: 1107 TGA
Molecular weight of protein: 26912.78
```
    1 GTA AAA TTC AGC GGG CGC TGA ATT GTA GAA GCC GAT CTA GAA GAG GGA   48

49 GAT GGA GGT GTC TAG GGG AAA GGG TGA CAT GTC TAT ATG AGG GTG GGG   96

97 GTG GGG TTG GTG TTG GTG ATG GTT GGA TAG TTG TTT GAG GTG TAG GTG  144

145 GGT AGA GGA GTG GGT GGG GTG TTG AAG ATA AAG GAG AAA AGT GCC GTC  192

193 GGG GCA CCT CCC AAC GCC ACC TTG GAA CAT TTC TAC CTG ACC AGT GGC  240

241 AAG CAG CCC AAG CAG GTG GAA GTA GAG CTT TTG TCC CGG CAG AGC GGG  288

289 CTC TCT GGC CGC CAG GTA GAG CGT TGG TTG CGT CGC CGC CGC AAC CAG  336

337 GAC CGG CCC AGT CTC CTC AAG AAG TTC CGA GAA GCC AGC TGG AGA TTC  384

385 ACA TTT TAC CTG ATT GCC TTC ATT GCC GGC ATG GCC GTC ATT GTG GAT  432

1 ........................................Met Ala Val Ile Val Asp   6

433 AAA CCC TGG TTC TAT GAC ATG AAG AAA GTT TGG GAG GGA TAT CCC ATA  480

7 Lys Pro Trp Phe Tyr Asp Met Lys Lys Val Trp Glu Gly Tyr Pro Ile  22

481 CAG AGC ACT ATC CCT TCC CAG TAT TGG TAC TAC ATG ATT GAA CTT TCC  528

23 Gln Ser Thr Ile Pro Ser Gln Tyr Trp Tyr Tyr Met Ile Gln Leu Ser  38

529 TTC TAC TGG TCC CTG CTC TTC AGC ATT GCC TCT GAT GTC AAG CGA AAG  576

39 Phe Tyr Trp Ser Leu Leu Phe Ser Ile Ala Ser Asp Val Lys Arg Lys  54

577 GAT TTC AAG GAA CAG ATC ATC CAC CAT GTG GCC ACC ATC ATT CTC ATC  624

55 Asp Phe Lys Glu Gln Ile Ile His His Val Ala Thr Ile Ile Leu Ile  70

625 AGC TTT TCC TGG TTT GCC AAT TAC ATC CGA GCT GGG ACT CTA ATC ATG  672

71 Ser Phe Ser Trp Phe Ala Asn Tyr Ile Arg Ala Gly Thr Leu Ile Met  86

673 GCT CTG CAT GAC TCT TCC GAT TAC CTG CTG GAG TCA GCC AAG ATG TTT  720

87 Ala Leu His Asp Ser Ser Asp Tyr Leu Leu Gln Ser Ala Lys Met Phe  102

721 AAC TAC GCG GGA TGG AAG AAC ACC TGC AAC AAC ATC TTC ATC GTC TTC  768

103 Asn Tyr Ala Gly Trp Lys Asn Thr Gys Asn Asn Ile Phe Ile Val Phe  118

769 GCC AAT GTT TTT ATC ATC ACC CGA CTG GTC ATC CTG CCC TTC TGG ATC  816
```

-continued

```
 119 Ala Ile Val Phe Ile Ile Thr Arg Leu Val Ile Len Pro Phe Trp Ile  134
 817 CTG CAT TGC ACC CTG GTG TAC CCA CTG GAG CTC TAT CCT GCC TTC TTT   864
 135 Leu His Cys Thr Leu Val Tyr Pro Leu Glu Leu Tyr Pro Ala Phe Phe  150
 865 GGC TAT TAC TTC TTC AAT TCC ATG ATG GGA GTT CTA CAG CTG CTG CAT   912
 151 Gly Tyr Tyr Phe Phe Asn Ser Met Met Gly Val Leu Gln Leu Leu His  166
 913 ATC TTC TCG CCC TAC CTC ATT TTG CGC ATG GCC CAC AAG TTC ATA ATC   960
 167 Ile Phe Trp Ala Tyr Leu Ile Leu Arg Met Ala His Lys Phe Ile Thr  182
 961 GGA AAG CTG GTA GAA GAT GAA CGC AGT GAC CGG-GAA GAA ACA GAG AGC  1008
 183 Gly Lys Leu Val Glu Asp Glu Arg Ser Asp Arg Glu Glu Thr Glu Ser  198
1009 TCA GAG GGG GAG GAG GCT GCA GCT GGG GGA GGA GCA AAG AGC CGG CCC  1056
 199 Ser Glu Gly Glu Glu Ala Ala Ala Gly Gly Gly Ala Lys Ser Arg Pro  214
1057 CTA GCC AAT GGC CAC CCC ATC CTC AAT AAC AAC CAT CGT AAG AAT GAC  1104
 215 Leu Ala Asn Gly His Pro Ile Leu Asn Asn Asn His Arg Lys Asn Asp  230
1105 TGA ACC ATT ATT CCA GCT GCC TCC CAG ATT AAT GCA TAA AGC CAA GGA  1152
 231 ***                                                              231
1153 ACT ACC CTG CTC CCT GCG CTA TAG GGT CAC TTT AAG CTC TGG GGA AAA  1200
1201 AGG AGA AAG TGA GAG GAG ACT TCT CTC CAT CCT CCC TCC TTG CTT GTC  1248
1249 ACC CAG TTG CCT TTA AAC CAA ATT CTA ACC AGC CTA TCC CCA GGT AGG  1296
1297 GGG GAC GTT GGT TAT ATT CTG TTA GAG GGG GAC GGT CGT ATT TTC CTC  1344
1345 CCT ACC CGC CAA GTC ATC CTT TCT ACT GCT TTT GAG GCC CTC CCT CAG  1392
1393 CTC TCT GTG GGT AGG GGT TAC AAT TCG CAT TCC TTA TTC TGA GAA TTT  1440
1441 GGC CCC AGC TGT TTG CCT TTG ACT CCC TGA CCT CCA GAG CCA GGG TTG  1488
1489 TGC CTT ATT GTC CCA TCT GTG GGC CTC ATT CTG CCA AAG CTG GAC CAA  1536
1537 GGC TAA CCT TTC TAA GCT CCC TAA CTT GGG CCA GAA ACC AAA GCT GAG  1584
1585 CTT TTA ACT TTC TCC CTC TAT GAC ACA AAT GAA TTG AGG GTA GGA GGA  1632
1633 GGG TGC ACA TAA CCC TTA CCC TAC CTC TGC CAA AAA GTG GCG GCT GTA  1680
1681 CTG GGG ACT GCT CGG ATG ATC TTT CTT AGT GCT ACT TCT TTC AGC TGT  1728
1729 CCC TGT AGC GAC AGG TCT AAG ATC TGA CTG CCT CCT TTC TCT GGC CTC  1776
1777 TTC CCC CTT CCC TCT TCT CTT CAG CTA GGC TAG CTG GTT TGG AGT AGA  1824
1825 ATG GCA ACT AAT TCT AAT TTT TAT TTA TTA AAT ATT TGG GGT TTT GGT  1872
1873 TTT AAA GCC AGA ATT ACG GCT AGC ACC TAG CAT TTC AGC AGA GGG ACC  1920
1921 ATT TTA GAC CAA AAT GTA CTG TTA ATG GGT TTT TTT TTA AAA TTA AAA  1968
1969 GAT TAA ATA AAA AAT ATT AAA TAA AAA AAA AAA AAA AAA               2007
```

D. Homology Comparison

The LAG1 Hs 2 cDNA clone of the invention contained full length cDNA sequence which shared 22% (41/185) identity and 43% (82/185) similarity in amino acid sequence with yeast Lag1 and shared 28% (54/191) identity and 46% (89/191) similarity with human LAG1 Hs.

(1) Homology comparison between LAG1 Hs 2 amino acid sequence and other related genes in yeast and *C. Elegans*
   Query=LAG 1 Hs 2 Sbjct=LAG1 Ce-1 (*C.Elegans*)
   >LAG1 Ce-1 length=368
   score=134 bits (334), expected=2e-36
   Identity71/194 (36%), Similarity=104/194 (53%), gap= 14/194 (7%)

```
Query:     3 VIVDKPWFYDMKKVWEGYPIQSTIPSQYWYYMIELSFYWSLLFSJASDVKRKDFKEQIIH    62
             V++   W YD+K+W GYP     +  +WYYMIE FY+SLL    DV+R DF +++H
Sbjct:   112 VMKNSSWLYDVKQCWIGYPFHPVPDTIWWYYMIETGFYYSLLIGSTFDVRRSDFWQLMVH   171

Query:    63 HVATTILISFSWFANYIRAGTLIMALHDSSDYLLESAKMFNY-AGWKNTCNNXXXXXXXX   121
             HV TI L+S SW   N++R GTLI+  HD SD LE  K+  Y A  KN   N
Sbjct:   172 HVITIFLLSSSVTINFVRVGTLILLSHDVSDVFLEGGKLVRYDAHNKNMTNFMFVLFFSS   231

Query:   122 XXXTRLVILPFWILHCT------------LVYPLELYPAFFGYYFFNSMMGVLQLLHIFW   169
                TRL+  PF ++               +++  +L P +         ++++L LHIFW
Sbjct:   232 WVATRLIYYPFIVIRSAVTEAAALIQPDYILWDYQLSPPYAPRLIVFALI-LLFFLHIFW   290

Query:   170 AYLILRMAHKFITG                                                183
             ++ILR+A++TG
Sbjct:   291 TFIILRIAYRTSTG                                                304
```

Query=LAG 1 Hs 2 Sbjct=Lag1Sc (yeast)
>Lag1Sc length=411
score=60.5 bits (144), expected=5e-14
Identity=42/185 (22%), Similarity=82/185 (43%), gap= 13/185 (7%)

vative motif in yeast Lag genes and the reported LAG1 Hs I (longevity assurance gene). Therefore, the LAG1 Hs 2 protein of the invention contained Lag1 motif, indicating that it might have the same or similar function with yeast longevity assurance proteins.

```
Query:     9 WFYDMKKVWEGYPIQSTIPSQYWYYMIELSFYWS---LLFSIASDVKRKDFKEQIIHHVA    65
             W  +  K ++ YP+  T P   +++  ++W+  +  +  +     RKD+KE +HH+
Sbjct:   200 WLFKTKPMYRTYPV-ITNPFLFKIFYLGQAAFWAQQACVLVLQLEKPRKDYKELVFHHIV   258

Query:    66 TIILISFSWFANYIRAGTLIMALHDSSDYLLESAKMFNYAGWKNTCNNXXXXXXXXXXXT   125
             T++LI   S+  +++G  I     D SD+L  +K NY         T
Sbjct:   259 TLLLIWSSYVFHFTKMGLAIYITMDVSDFFLSLSKTLNYLNSVFTPFVFGLFVFFWIYLR   318

Query:   126 RLV-ILPFWIL--------HCTLVYPLELYPAFFGYYFFNSMMGVLQLLHIFWAYLILRM   176
             +V  i   W +         +L +  +Y +           ++ LQL++++W +LILR+
Sbjct:   319 HVVNIRILWSVLTEFRHEGNYVLNFATQQYKCWISLPIVFVIAALQLVNLYWLFLILRI   378

Query:   177 AHKFI                                                         181
             ++ I
Sbjct:   379 LYRLI                                                         383
```

(2) Homology comparison between LAG1Hs 2 amino acid sequence and human LAG1Hs:
>Lag1Hs length=350
score=77.3 bits (187), expected=4e-19
Identity=54/191 (28%), Similarity=89/191 (46%), gap= 11/191 (5%)

EXAMPLE 3

Inhibitory Effect of LAG1 Hs 2 on the Growth of Transplanting Human Hepatocarcinoma in Nude Mice Body in vivo inhibit the growth of tumor in nude mice.

```
Query:     6 DKPWFYDMKKVWEGYPIQSTIPSQYWY-YMIELSFYW-SLLFSIASDVKRKDFKEQIIHH    63
             D P+F+D  V+  +     +P    Y+++SFY  S+  ++ D  RKD     ++HH
Sbjct:   124 DYPFFHDPPSVFYDWTPGMAVPRDIAAAYLLQGSFYGHSIYATLYMDTWRKDSVVMLLHH   183

Query:    64 VATIILISFSWFANYIRAGTLIMALHDSSDYLLESAKMFNYAGWKNTCNNXXXXXXXXXX   123
             V T+ILI  S+     Y  G L++LHD SD LE  K+Y   +   +
Sbjct:   184 VVTLILIVSSYAFRYHNVGILVLFLHDISDVQLEFTKLNIYFKSRGGSYHRLHALAADLG   243

Query:   124 -----------RLVILPFWILHCTLVYPLELYPAFFGYYFFNSMMGVLQLLHIFWAYLIL   174
                        RL  P  +L+T  L P    Y+FFN++++L L++++W   I+
Sbjct:   244 CLSFGFSWFWFRLYWFPLKVLYATSHCSLRTVPDIPFYFFFNALLLLLTLMNLYWFLYIV   303

Query:   175 RMAHKFITGKL                                                   185
              A K  +TG++
Sbjct:   304 AFAAKVLTGQV                                                   314
```

F: Motif Analysis

Figures 1, 2, 3:
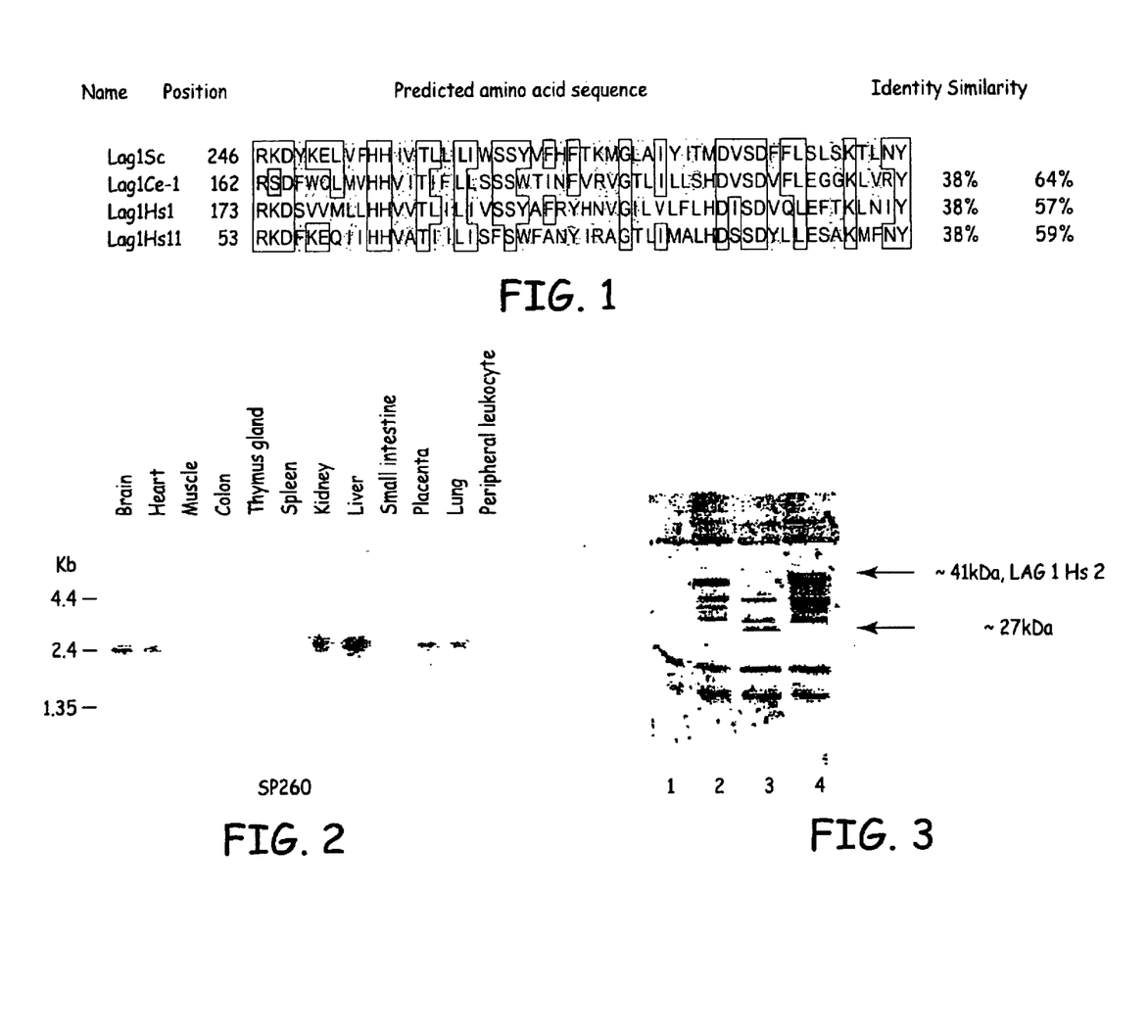
FIG. 1 shows the alignment of Lag1 motif in the four proteins: Lag1Sc, Lag1Cel, Lag1 Hs1, and Lag1 Hs2 of the invention Lag1.
FIG. 2 shows the expression of Lag1 Hs2.
FIG. 3 shows the gel electrophoresis result of Lag1 Hs2 expressed in the *E. Coli* T7 S30 in vitro translation system.

As shown in FIG. 1, the LAG1 Hs 2 cDNA sequence of the invention contained a signature sequence (RKDFKEQIIHHVATIILISFSWFANYIRA GTLIMALHDSSDYLLESAKMFNY) at position 53-104 of the amino acid sequence, which was highly homologous to the yeast Lag1P motif, which was a common and conser- The human hepatocarcinoma was transplanted s.c. into nude mice. After the diameter of tumor was about 0.5 cm (about 1 week), the mice were randomly divided into groups with 6 mice per group. One group was the control group, i.e., the saline group. One group was the experiment group, in which LAG1 Hs2 gene was cloned into eukaryotic expression vector pBKCMV to form expression plasmid. In the control group, the mice were injected around the tumor with 100 μl physiological saline per time per week. In the experiment group, the mice were injected around the tumor with 100 μl physiological saline containing 0.2 ug LAG1 Hs2 expression plasmid packed within GE7 gene transferring system per time per week. The total number of injection was 4. One week after the last injection, the nude mice were sacrificed and tumors were taken out and weighted for statistics analysis and calculating ±SD. The results were shown in the following table. LAG1 Hs2 gene showed a 29.4% inhibition rate.

|  | $\overline{W}$ ± SD | Inhibition rate |
|---|---|---|
| Control | 4.01 ± 0.53 |  |
| LAG1 Hs2 | 2.83 ± 1.55 | 29.4% |

EXAMPLE 4

Expression of LAG1 Hs2 in Various Human Tissues

The LAG1 Hs2 gene was used as a probe and hybridized with multi-tissue mRNA membrane (CLONTECH™). The results were shown in FIG. 2. The Northern hybridization indicated that LAG1 Hs2 gene had high level of mRNA expression in kidney, livery tissue, low expression in brain, heart, placenta, and lung, and no expression in muscle, colon, thymus gland, spleen, small intestine, and peripheral leukocyte.

In situ hybridization results indicated that, compared with hepatocarcinoma tissue, the expression of LAG1 Hs2 in normal liver was higher than that in the noncancerous liver tissue, and the expression of LAG1 Hs2 in noncancerous liver tissue was higher than that in the cancerous liver tissue. Therefore, the expression of said gene was proved to be down-regulated in human hepatocarcinoma.

EXAMPLE 5

Expression of LAG1 Hs2 Protein in an in vitro Translation System (1) Cloning LAG1 Hs2 Gene into an Expression Vector Containing T7 Promotor In this example, both non-fusion expression and fusion expression were utilized. In non-fusion expression, a pair of specific primers were designed for the ORF of LAG 1 Hs2 gene. The 5' end primer contained a NcoI site, and the 3' end primer contained a HindIII site. The LAG 1 Hs2 clone plasmid or the amplified products in RT-PCR were used as templates to amplify fragments by PCR. The product was cut with NcoI and HindIII. The plasmid for non-fusion expression was p22450 containing T7 promotor (Said vector was constructed by the Shanghai biological engineering center, CAS). The vector was cut with NcoI and HindIII and linked with digested PCR fragment to form the plasmid for non-fusion expression.

In fusion expression, a pair of specific primers were designed for the ORF of LAG 1 Hs2 gene. The 5' end primer contained an EcoRI site, and the 3' end primer contained a HindIII site. The LAG 1 Hs2 clone plasmid or the amplified products in RT-PCR were used as templates to amplify fragments by PCR. The product was cut with EcoRI and HindIII. The vector for fusion expression was pT7zza (Said vector was constructed by the Shanghai biological engineering center, CAS). The vector was cut with EcoRI and HindIII and linked with digested PCR fragment to form the plasmid for fusion expression.

(2) in vitro Expression and Translation

The two above constructed expression plasmid was utilized together with *E. coli* T7 S30 Exact System for Circular DNA (Promega, Cat #L1130) and TRANSCEND™ Colorimetric Translation Detection System (Promega, Cat. #L5070) so as to in vitro express LAG1 Hs2 protein.

| 1. Formulating in vitro translation system: | |
|---|---|
| Plasmid DNA: | 1–4 μg |
| Complete mixture of amino acids and tRNA: | 5 μl |
| S30 pre-mixture (amino acid free): | 20 μl |
| TRANSCEND ™ tRNA*: | 1 μl |
| T7S30 cell lysate: | 15 μl |
| Sterilized water containing no nuclease (add to final concentration): | 50 μl |

*TRANSCEND ™ tRNA was Lys-tRNA in which e-$NH_2$ was labeled with biotin.

Incubating at 37° C. for 1–2 hours.

2. Analysis of in vitro translation products:

SDS-PAGE analysis: 15% separation gel, 4% concentrated gel.

Electro-transferring to PVDF: 100V, 60 min.

Streptavidin-alkaline phosphatase was used to bind the translated protein which contained biotin. Then the Western blue stabilized substrate for alkaline phosphatase was used to develop the color.

The results showed that the positive control of CAT fusion expression plasmid had a protein band at 39 KD, and LAG1 Hs2 expression plasmid pT7X-LAG1 Hs2 had a protein band at 27 KD. The LAG1 Hs2 protein fusion expression plasmid pT2Zza-LAG1 Hs2 had a protein band at 41 KD. The molecular weight matched the prediction (FIG. 3), thus indicating the LAG1 Hs2 protein was expressed in in vitro translation system.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

What is claimed is:

1. An isolated polynucleotide wherein said polynucleotide sequence has a length of 690 bp and encodes a polypeptide which consists of the amino acid sequence of SEQ ID NO: 2.

2. The polynucleotide of claim 1 which is consists of the nucleotide sequence of position 415–1104 of SEQ ID NO: 3.

3. A vector containing the polynucleotide of claim 1.

4. A genetically engineered host cell which is selected from the group consisting of:

(a) a host cell transformed with the vector of claim 3, and (b) a host cell transformed with the polynucleotide of claim 1.

5. A method for producing longevity assurance protein, which comprises:

(a) culturing the host cell of claim 4 under the conditions suitable for the expression of protein;

(b) isolating the longevity assurance protein from the culture.

* * * * *